(12) United States Patent
Petereit et al.

(10) Patent No.: US 8,465,769 B2
(45) Date of Patent: Jun. 18, 2013

(54) PHARMACEUTICAL COMPOSITION WITH CONTROLLED ACTIVE INGREDIENT RELEASE FOR ACTIVE INGREDIENTS WITH GOOD SOLUBILITY IN WATER

(75) Inventors: Hans-Ulrich Petereit, Darmstadt (DE); Hema Ravishankar, Chembur (IN); Shradda Bodinge, Mumbai (IN)

(73) Assignee: Evonik Roehm GmbH, Darmstadt (DE)

( * ) Notice: Subject to any disclaimer, the term of this patent is extended or adjusted under 35 U.S.C. 154(b) by 1170 days.

(21) Appl. No.: 11/695,848

(22) Filed: Apr. 3, 2007

(65) Prior Publication Data

US 2008/0044470 A1    Feb. 21, 2008

(30) Foreign Application Priority Data

Aug. 18, 2006 (IN) .............. 1465/CHE/2006

(51) Int. Cl.
*A61K 9/48*    (2006.01)
(52) U.S. Cl.
USPC .......................................................... 424/463
(58) Field of Classification Search
None
See application file for complete search history.

(56) References Cited

U.S. PATENT DOCUMENTS

| 4,663,150 | A | * | 5/1987 | Panoz et al. .................. 424/494 |
| 5,395,628 | A | * | 3/1995 | Noda et al. .................... 424/490 |
| 6,368,628 | B1 | * | 4/2002 | Seth ............................... 424/480 |
| 6,878,387 | B1 | | 4/2005 | Petereit et al. |
| 2006/0183767 | A1 | * | 8/2006 | Mandrea ..................... 514/292 |
| 2008/0200401 | A1 | * | 8/2008 | Addington .................... 514/23 |

FOREIGN PATENT DOCUMENTS

| DE | 198 45 358 A1 | 4/2000 |
| DE | 10 2004 035 938 A1 | 2/2006 |
| EP | 0 436 370 A1 | 7/1991 |
| EP | 1 157 690 A1 | 11/2001 |
| EP | 1 213 015 A1 | 6/2002 |

OTHER PUBLICATIONS

Office Action issued Dec. 15, 2010, in Israeli Patent Application No. IL 195407, filed Sep. 21, 2006 (with English translation).

* cited by examiner

*Primary Examiner* — Paul Dickinson
(74) *Attorney, Agent, or Firm* — Oblon, Spivak, McClelland, Maier & Neustadt, L.L.P.

(57) ABSTRACT

A pharmaceutical preparation comprising:
a) a core with an active ingredient and with an organic acid and/or the salt of an organic acid; and
b) a coating which envelops the core and which comprises a polymer content of (meth)acrylate copolymers which have not more than 15% by weight of cationic or anionic groups, and which comprises at least 60% by weight of a (meth)acrylate copolymer which is composed of free-radically polymerized units of 93 to 98% by weight $C_1$- to $C_4$-alkyl esters of acrylic or of methacrylic acid and 7 to 2% by weight (meth)acrylate monomers having a quaternary ammonium group in the alkyl radical, wherein the active ingredient has a solubility in water of at least 10 g/l at 20° C. and the coating comprises silicon dioxide particles having an average particle size in the range from 1 to 50 μm.

24 Claims, No Drawings

PHARMACEUTICAL COMPOSITION WITH CONTROLLED ACTIVE INGREDIENT RELEASE FOR ACTIVE INGREDIENTS WITH GOOD SOLUBILITY IN WATER

CROSS-REFERENCE TO RELATED APPLICATION

This application claims priority to IN 1465/CHE/2006, filed Aug. 18, 2006 which is hereby incorporated by reference.

FIELD OF THE INVENTION

The invention relates to the field of pharmaceutical compositions with controlled active ingredient release for active ingredients with good solubility in water.

PRIOR ART

EP-A 0 463 877 describes pharmaceutical compositions with delayed active ingredient release consisting of a core with an active pharmaceutical ingredient and a monolayer coating film which comprises a water-repellent salt and a water-insoluble copolymer of ethyl acrylate, methyl methacrylate and trimethylammoniumethyl methacrylate chloride. The water-repellent salt may be for example Ca stearate or Mg stearate. Sigmoidal release plots are obtained.

EP-A 0 225 085, EP-A 0 122 077 and EP-A 0 123 470 describe the use of organic acid in medicament cores which are provided with various coatings from organic solutions. Essentially sigmoidal release characteristics result. EP-A 0 436 370 describes pharmaceutical compositions with delayed active ingredient release consisting of a core with an active pharmaceutical ingredient and an organic acid and an outer coating film which has been applied by aqueous spraying and is a copolymer of ethyl acrylate, methyl methacrylate and trimethylammoniumethyl methacrylate chloride. In this case, sigmoidal release plots are likewise obtained.

EP 1 117 387 B1 describes a similar system to EP-A 0 436 370. The essential difference is the use of the organic acids in salt form, it thus being possible to have a beneficial influence in particular on the duration of the lag phase and on the steepness of the sigmoidal release plots. Possible processing aids which are mentioned are inter alia ground silica and pore formers.

PROBLEM AND SOLUTION

With a large number of pharmaceutical forms and active ingredients it is therapeutically worthwhile to have sigmoidal release characteristics with an initial phase with delayed active ingredient release (lag phase), a subsequent main release phase (pulse phase) and a run-out phase. The general intention is that active ingredient release in the lag phase is as low as possible and active ingredient release in the subsequent pulse phase is as fast as possible. This aim is achieved in part by the technical teachings of EP-A 0 436 370 and EP 1 117 387 B1. In EP 1 117 387 B1, good results are achieved in particular with sodium acetate. There is, however, a continual need for improvement. One problem was regarded as being to develop further the pharmaceutical preparations with sigmoidal active ingredient release which are disclosed in EP-A 0 436 370 and EP 1 117 387 B1 in order to come closer to the aims mentioned above.

The problem has been solved by a pharmaceutical preparation comprising:
  a) a core with an active ingredient and with an organic acid and/or the salt of an organic acid,
  b) a coating which envelops the core and which comprises a polymer content of (meth)acrylate copolymers which have not more than 15% by weight of cationic or anionic groups, and which comprises at least 60% by weight of a (meth)acrylate copolymer which is composed of free-radically polymerized units of 93 to 98% by weight $C_1$- to $C_4$-alkyl esters of acrylic or of methacrylic acid and 7 to 2% by weight (meth)acrylate monomers having a quaternary ammonium group in the alkyl radical, characterized in that:
  the active ingredient has a solubility in water of at least 10 g/l at 20° C. and
  the coating comprises silicon dioxide particles having an average particle size in the range from 1 to 50 µm.

The ranges described above include all intermediate values and subranges.

IMPLEMENTATION OF THE INVENTION

Cores (a)

In the simplest case, the core can be composed only of the active ingredient and of the organic acid and/or the salt of the organic acid, but ordinarily it additionally comprises a carrier, e.g. a nonpareil, and pharmaceutical excipients such as, for example, colloidal silica or polyvinylpyrrolidone (PVP).

The core (a) can consist for example of:
  active ingredient in an amount of 97.5 to 2.5, preferably 80 to 5, % by weight based on the weight of the core
  an organic acid and/or one or more salts of organic acids in an amount of 2.5 to 97.5, preferably 5 to 80, in particular 10 to 50, % by weight based on the weight of the core
  optionally pharmaceutical excipients in an amount of 0-95, preferably 10 to 50, % by weight based on the weight of the core
  optionally a carrier with a proportion of the core weight of 0 to 95, preferably 10 to 50, % by weight.

The ranges described above include all intermediate values and subranges.

The cores can be produced for example by direct compression, extrusion and subsequent rounding off, wet or dry granulation or direct pelletizing (e.g. on discs) or by binding of powders (powder layering) onto active ingredient-free beads (nonpareils) or active ingredient-containing particles.

The pharmaceutical excipients which are contained in addition to the active ingredient may be for example binders such as cellulose and derivatives thereof, polyvinylpyrrolidone (PVP), gelatin, (meth)acrylates, starch and derivatives thereof or sugars.

The cores may be homogeneous or have a layered structure, in which case the active ingredient is preferably located in the outer layer. It is particularly preferred for the organic acid and/or the salt of the organic acid to form the outer layer of the core.

Organic Acids

The organic acids employed must be toxicologically acceptable and usable in medicaments. The preferred type depends on the specific formulation. Organic acids such as citric acid, fumaric acid, formic acid, succinic acid, acetic acid, maleic acid, tartaric acid, glutaric acid or lactic acid are preferred.

Succinic acid is particularly suitable for the purposes of the invention. Citric acid is in principle likewise suitable, although the release profiles obtained in buffered media which approximately correspond to physiological conditions are not so steep as with succinate. Acetic acid may occasionally lead to stability problems which may appear during storage of the pharmaceutical forms. No such problems are known as yet on use of succinic acid.

The type of acid controls the steepness of the active ingredient release plot especially in sigmoidal release plots.

The organic acids may be present in the formulations according to the invention preferably as outer layer of the core, bound by binders. They can be applied by spraying on from solution or by powder application with simultaneous addition of binder solution.

However, in individual cases, variants in which the active ingredient is applied in a mixture with organic acids, or a sealing layer is applied between the active ingredient layer and the salt layer, are also worthwhile. The organic acid can also be applied last to the core, so that it forms the outer layer.

The amount of the organic acid(s) as a proportion of the weight of the core may be 2.5% by weight to 97.5% by weight, preferably 5 to 80% by weight, in particular 10-50% by weight.

The ranges described above include all intermediate values and subranges.

Salts of Organic Acids:

Salts of organic acids are preferred to the organic acids. In most cases, a smaller active ingredient release during the lag phase and subsequently a faster active ingredient release is observed on use of the organic acids in salt form compared with the organic acids.

The employed salts of organic acids must be toxicologically acceptable and usable in medicaments. Alkali metal salts (ammonium, lithium, sodium, potassium) are preferred. The preferred type depends on the specific formulation; besides the functionality according to the invention, however, the pharmacological effects of the ions must also be taken into account. Salts of weak organic acids such as succinic acid, citric acid, fumaric acid, formic acid, acetic acid, maleic acid, tartaric acid, glutaric acid or lactic acid are preferred.

Sodium succinate is particularly suitable for the purposes of the invention. Sodium citrate is in principle likewise suitable, although the release profiles obtained in buffered media which approximately correspond to physiological conditions are not so steep as with sodium succinate. Sodium acetate may occasionally lead to stability problems which may appear during storage of the pharmaceutical forms. No such problems are known as yet on use of sodium succinate.

The type of acid controls the steepness of the active ingredient release plot especially in sigmoidal release plots.

The salts may be present in the formulations according to the invention as outer layer of the core, bound by binders. They can be applied by spraying on from solution or by powder application with simultaneous addition of binder solution.

However, in individual cases, variants in which the active ingredient is applied in a mixture with the salts, or a sealing layer is applied between the active ingredient layer and the salt layer, are also worthwhile. The salt of the organic acid can also be applied last to the core, so that it forms the outer layer.

The amount of the salts of the organic acid(s) as a proportion of the weight of the core may be 2.5% by weight to 97.5% by weight, preferably 5 to 80% by weight, in particular 10-50% by weight.

The ranges described above include all intermediate values and subranges.

Coating b)

The coating b) consists of one or more (meth)acrylate copolymers, $SiO_2$ particles, and where appropriate conventional pharmaceutical excipients such as, for example, plasticizers, pigments, wetting agents, mould release agents etc. The outer coating preferably envelops the core directly without further layers being present between the core and the coating film.

The polymer content of the coating is converted into a film together with the contained $SiO_2$ particles and further excipients such as, for example, plasticizers which are present where appropriate, and forms a continuous coating or coating film. The coating or coating film in its entirety controls, together with the organic acid and/or salts thereof present in the core, the active ingredient delivery.

Polymer Content of the Coating b)

The polymer content of the coating b) comprises at least 60% by weight, preferably 85 to 95% by weight, one or optionally also more (meth)acrylate copolymers from free-radically polymerized monomer units consisting of 93 to 98% by weight $C_1$- to $C_4$-alkyl esters of acrylic or of methacrylic acid and 7 to 2% by weight (meth)acrylate monomers having a quaternary ammonium group in the alkyl radical (EUDRAGIT® RS type). The polymer content of the coating may also where appropriate consist 100% of the foregoing polymer type.

The polymer content of the coating may amount preferably to 10 to 200, preferably 20 to 100, % by weight based on the weight of the core.

The polymer content of the coating based on the coating should amount to at least 50% by weight. The coating may where appropriate consist only of the said (meth)acrylate copolymers and the $SiO_2$ content. However, usually, the coating will comprise in addition to the $SiO_2$ content further pharmaceutically usual additives such as, for example, plasticizers or pigments.

The principle of the invention is based on a presumed interaction between the essential ingredients of the core and the essential ingredients of the coating.

The effect according to the invention surprisingly occurs only with active ingredients which have a solubility in water of at least 10 g/l, preferably at least 30 g/l, more preferably at least 100 g/l. In order to ensure this interaction, the said (meth)acrylate copolymer is to be at least 50% by weight involved in the structure of the coating in order to achieve the desired interaction. Such (meth)acrylate copolymers are commercially available and have been used for a long time for release-slowing coatings. They are practically insoluble in water. They can be used alone or in a mixture with other (meth)acrylate copolymers.

In order to achieve according to the invention sigmoidal active ingredient release characteristics, the polymer content of the coating b) should consist of at least 60, preferably at least 85, % by weight or 100% by weight of the said copolymer type (Eudragit® RS type).

Preferred $C_1$- to $C_4$-alkyl esters of acrylic or of methacrylic acid are methyl acrylate, ethyl acrylate, butyl acrylate, butyl methacrylate and methyl methacrylate.

The particularly preferred (meth)acrylate monomer having a quaternary ammonium group is 2-trimethylammoniumethyl methacrylate chloride.

A corresponding copolymer can be composed for example of 50-70% by weight methyl methacrylate, 20-40% by weight ethyl acrylate and 7-2% by weight trimethylammoniumethyl methacrylate chloride.

A preferred copolymer comprises 65% by weight methyl methacrylate, 30% by weight ethyl acrylate and 5% by weight 2-trimethylammoniumethyl methacrylate chloride (EUDRAGIT® RS).

The ranges described above include all intermediate values and subranges.

Mixtures of (Meth)Acrylate Copolymers

The polymer content of the coating may also be in the form of a mixture of (meth)acrylate copolymers. The (meth)acrylate copolymers used in addition for the mixture should have not more than 15% by weight of cationic or anionic groups. With a content of more than 15% by weight cationic or anionic groups, i.e. basic groups or acidic groups, in the alkyl radical, the interactions of the components with one another are influenced in an unwanted or scarcely predictable manner.

In the case of a mixture, the proportion of the (meth)acrylate copolymer from free-radically polymerized monomer units consisting of 93 to 98% by weight $C_1$- to $C_4$-alkyl esters of acrylic or of methacrylic acid and 7 to 2% by weight (meth)acrylate monomers having a quaternary ammonium group in the alkyl radical (EUDRAGIT® RS type) is at least 60, preferably 85 to 95, % by weight, in each case based on the weight of the core. The proportion of the admixed polymer(s) is up to 40% by weight, preferably 5-15% by weight, with the proportions of the mixed polymers adding up to 100% by weight.

A suitable (meth)acrylate copolymer for a mixture may be composed for example of free-radically polymerized monomer units of 85 to less than 93% by weight $C_1$- to $C_4$-alkyl esters of acrylic or of methacrylic acid and more than 7 to 15% by weight (meth)acrylate monomers having a quaternary ammonium group in the alkyl radical. Such (meth)acrylate copolymers are commercially available and have been used for a long time for release-slowing coatings (EUDRAGIT® RL type). The proportion in the mixture can be up to 40% by weight, preferably 5 to 15% by weight.

A specifically suitable copolymer for a mixture comprises for example 60% by weight methyl methacrylate, 30% by weight ethyl acrylate and 10% by weight 2-trimethylammoniumethyl methacrylate chloride (EUDRAGIT® RL).

A further suitable (meth)acrylate copolymer for a mixture consists of 95 to 100, in particular more than 95 to 100, % by weight $C_1$- to $C_4$-alkyl esters of acrylic or of methacrylic acid and up to 5% by weight, or 0 to 5, in particular 0 to less than 5, % by weight acrylic or methacrylic acid. Such (meth)acrylate copolymers are commercially available (EUDRAGIT® NE type).

The (meth)acrylate copolymer content of the outer coating film b) may be for example a mixture of:

60 to 99, preferably 85 to 95, % by weight of a (meth)acrylate copolymer which consists of 93 to 98% by weight $C_1$- to $C_4$-alkyl esters of acrylic or of methacrylic acid and 2 to 7% by weight (meth)acrylate monomers having a quaternary ammonium group in the alkyl radical, and 1-40, preferably 5 to 15, % by weight of a (meth)acrylate copolymer which is composed of 85 to less than 93% by weight $C_1$- to $C_4$-alkyl esters of acrylic or of methacrylic acid and more than 7 to 15% by weight (meth)acrylate monomers having a quaternary ammonium group in the alkyl radical.

Preferred $C_1$- to $C_4$-alkyl esters of acrylic or of methacrylic acid are methyl acrylate, ethyl acrylate, butyl acrylate, butyl methacrylate and methyl methacrylate.

The particularly preferred (meth)acrylate monomer having a quaternary ammonium group is 2-trimethylammoniumethyl methacrylate chloride.

The ranges described above include all intermediate values and subranges.

Preparation of the (Meth)Acrylate Copolymers in General

The (meth)acrylate copolymers can be obtained in a manner known per se by free-radical bulk, solution, bead or emulsion polymerization. They may be in the form of, for example, extruded granules, ground powder, solution or dispersion.

Coatings

The polymer application depends on the size and surface of the cores, on the solubility of the active ingredients and on the desired release profile. The polymer content of the coating based on the weight of the core can be 10 to 200, preferably 15 to 100, % by weight.

The coatings can be applied in a plurality of layers or as mixture. Mixtures of the polymers allow particular gradients to be set in the second phase of the release profile. The content of quaternary ammonium groups in the coating controls the permeability and thus the diffusion rate of dissolved substances (McGinity, Ed., Aqueous Polymeric Coatings for Pharmaceutical Dosage Forms, Marcel Dekker, Inc., Chapter 4, pp. 208-216). A higher proportion of hydrophilic quaternary ammonium groups means a faster release rate. An additional possibility for controlling active ingredient delivery in the second phase of the release profile is attained in this way.

The ranges described above include all intermediate values and subranges.

Additional Outer Layers

The preparation according to the invention may additionally be enveloped by a (meth)acrylate copolymer which comprises 5-60% by weight methacrylic acid residues. It is possible in this way to provide the preparation with a covering which is resistant to gastric juice but soluble in intestinal juice.

Also suitable are anionic (meth)acrylate copolymers composed of 40 to 60% by weight methacrylic acid and 60 to 40% by weight methyl methacrylate or 60 to 40% by weight ethyl acrylate (EUDRAGIT® L or EUDRAGIT® L100-55 types).

EUDRAGIT® L is a copolymer of 50% by weight methyl methacrylate and 50% by weight methacrylic acid.

EUDRAGIT® L 100-55 is a copolymer of 50% by weight ethyl acrylate and 50% by weight methacrylic acid. EUDRAGIT® L 30D-55 is a dispersion comprising 30% by weight EUDRAGIT® L 100-55.

Likewise suitable are anionic (meth)acrylate copolymers composed of 20 to 40% by weight methacrylic acid and 80 to 60% by weight methyl methacrylate (EUDRAGIT® S type).

Particularly suitable are (meth)acrylate copolymers consisting of 10 to 30% by weight methyl methacrylate, 50 to 70% by weight methyl acrylate and 5 to 15, preferably 8 to 12, % by weight methacrylic acid (EUDRAGIT® FS type).

EUDRAGIT® FS is a copolymer of 25% by weight methyl methacrylate, 65% by weight methyl acrylate and 10% by weight methacrylic acid. EUDRAGIT® FS 30 D is a dispersion comprising 30% by weight EUDRAGIT® FS.

Additionally suitable for the purposes of the invention is a copolymer (see WO 2003/072087) which is composed of 20 to 34% by weight methacrylic acid and/or acrylic acid,
   20 to 69% by weight methyl acrylate and
   0 to 40% by weight ethyl acrylate and/or where appropriate
     0 to 10% by weight further monomers capable of vinylic copolymerization, with the proviso that the glass transition temperature of the copolymer according to ISO 11357-2, subclause 3.3.3, is not more than 60° C. This (meth)acrylate copolymer is particularly suitable, because of its good elongation at break properties, for compressing pellets to tablets.

The copolymer is in particular composed of free-radically polymerized units of 20 to 34, preferably 25 to 33, particularly preferably 28 to 32, % by weight methacrylic acid or acrylic acid, with preference for methacrylic acid, 20 to 69, preferably 35 to 65, particularly preferably 35 to 55, % by weight methyl acrylate and where appropriate
0 to 40, preferably 5 to 35, particularly preferably 15 to 35, % by weight ethyl acrylate, with the proviso that the glass transition temperature of the copolymer (measurement without added plasticizer with a residual monomer content (REMO) of less than 100 ppm, heating rate 10° C./min, nitrogen atmosphere) according to ISO 11357-2, subclause 3.3.3 ($T_{mg}$), is not more than 60, preferably 40 to 60, particularly preferably 45 to 55° C.

The copolymer preferably consists substantially to exclusively of the monomers methacrylic acid, methyl acrylate and ethyl acrylate in the quantitative proportions indicated above.

However, it is possible in addition, without leading to an impairment of the essential properties, for small amounts in the range from 0 to 10, e.g. 1 to 5, % by weight of further monomers capable of vinylic copolymerization, such as, for example, methyl methacrylate, butyl methacrylate, butyl acrylate or hydroxyethyl methacrylate, to be present.

It is also possible to employ mixtures of the said copolymers to adjust specific release profiles or release sites.

Glass transition temperature means here in particular the midpoint temperature $T_{mg}$ specified in ISO 11357-2, subclause 3.3.3. The measurement takes place without added plasticizer, with residual monomer contents (REMO) of less than 100 ppm, with a heating rate of 10° C./min and under a nitrogen atmosphere.

The copolymers are obtained in a manner known per se by free-radical bulk, solution, bead or emulsion polymerization. They must be brought before processing into the particle size range according to the invention by suitable grinding, drying or spraying processes. This can take place by simple crushing of extruded and cooled pellets or hot cut.

The use of powders may be advantageous, especially in the case of mixing with further powders or liquids. Suitable items of apparatus for producing the powders are familiar to the skilled person, e.g. air jet mills, pin disc mills, compartment mills. It is possible where appropriate to include appropriate sieving steps. A suitable mill for industrial large quantities is for example an opposed jet mill (Multi No. 4200) which is for example operated with a pressure of about 6 bar.

Additionally suitable for the purposes of the invention are copolymers (see WO 2004/096185) composed of:
20 to 33% by weight methacrylic acid and/or acrylic acid,
5 to 30% by weight methyl acrylate and
20 to 40% by weight ethyl acrylate and
more than 10 to 30% by weight butyl methacrylate and where appropriate
0 to 10% by weight further monomers capable of vinylic copolymerization, where the proportions of the monomers add up to 100% by weight,
with the proviso that the glass transition temperature of the copolymer according to ISO 11357-2, subclause 3.3.3 (midpoint temperature $T_{mg}$), is 55 to 70° C. Copolymers of this type are particularly suitable, because of their good mechanical properties, for compressing pellets to tablets.

The abovementioned copolymer is composed in particular of free-radically polymerized units of:
20 to 33, preferably 25 to 32, particularly preferably 28 to 31, % by weight methacrylic acid or acrylic acid, with preference for methacrylic acid,
5 to 30, preferably 10 to 28, particularly preferably 15 to 25, % by weight methyl acrylate,
20 to 40, preferably 25 to 35, particularly preferably 28 to 32, % by weight ethyl acrylate, and
more than 10 to 30, preferably 15 to 25, particularly preferably 18 to 22, % by weight butyl methacrylate,
where the monomer composition is chosen so that the glass transition temperature of the copolymer is 55 to 70° C., preferably 59 to 66, particularly preferably 60 to 65° C.

It is also possible to employ mixtures of the said copolymers to adjust specific release profiles or release sites.

Glass transition temperature means here in particular the midpoint temperature $T_{mg}$ specified in ISO 11357-2, subclause 3.3.3. The measurement takes place without added plasticizer, with residual monomer contents (REMO) of less than 100 ppm, with a heating rate of 10° C./min and under a nitrogen atmosphere.

The copolymer preferably consists substantially to exclusively, to the extent of 90, 95 or 99 to 100% by weight, of the monomers methacrylic acid, methyl acrylate, ethyl acrylate and butyl methacrylate in the quantitative ranges indicated above.

It is, however, in addition possible, without necessarily leading to an impairment of the essential properties, for small amounts in the range from 0 to 10, e.g. 1 to 5, % by weight of further monomers capable of vinylic copolymerization, such as, for example, methyl methacrylate, butyl acrylate, hydroxyethyl methacrylate, vinylpyrrolidone, vinylmalonic acid, styrene, vinyl alcohol, vinyl acetate and/or derivatives thereof to be present.

The ranges described above include all intermediate values and subranges.

Silicon Dioxide Particles

The coating which envelops the core comprises silicon dioxide particles having an average particle size in the range from 1 to 50 µm. The silicon dioxide particles present in the coating also assume the function as non-stick agent. The effect according to the invention, in particular a shortening of the pulse phase to less than 4 hours, occurs on use as claimed of this type of particles in the coating. On use of $SiO_2$ particles of different average particle size or on use of other mould release agents such as, for example, talc or glycerol monostearate (GMS) on their own, the advantageous effects of the invention surprisingly do not appear to occur (see the examples).

The coating comprises silicon dioxide particles ($SiO_2$ particles) having an average particle size d50, which can be measured for example by means of laser diffraction according to ISO 13320-1, in the range from 1 to 50, preferably from 1 to 30, particularly preferably 1 to 10, µm. The best results are achieved with precipitated and ground $SiO_2$, e.g. produced by the sol-gel process. This type of silicon dioxide is also designated according to the German pharmacopoeia, DAB 1999, as *Silicii dioxidium praecipitatum*. Preference is given of course to products or silicon dioxide particles of proven pharmaceutical quality or in pharmaceutical quality which comply with the requirements of DAB 1999 in respect of purity.

Unsuitable for the purposes of the invention is colloidal $SiO_2$ of the Aerosil® type, which is produced by a flame process and usually has average particle sizes in the range below 100 nm. The latter can, however, be employed uncritically for example as excipient for formulating the cores.

Preferred amounts employed of the silicon dioxide particles are 5 to 50, particularly preferably 10 to 40, and especially 10 to 30, % by weight $SiO_2$ based on the dry weight of the (meth)acrylate copolymer(s) in the coating.

The ranges described above include all intermediate values and subranges.

Further Pharmaceutically Usual Excipients

The core and/or the coating may comprise further pharmaceutically usual excipients.

Further additives serve in particular as processing aids and are intended to ensure a reliable and reproducible production process and good long-term storage stability. They may influence the permeability of the coatings, which can be utilized where appropriate as additional control parameter.

The cores can be produced for example by direct compression, extrusion and subsequent rounding off, wet or dry granulation or direct pelletization (e.g. on discs) or by binding of powders (powder layering) onto active ingredient-free beads (nonpareils) or active ingredient-containing particles. The pharmaceutical excipients which are present in addition to the active ingredient may be for example binders such as cellulose and derivatives thereof, polyinylpyrrolidone (PVP), gelatin, (meth)acrylates, starch and derivatives thereof or sugars.

Plasticizers:

Plasticizers may be present in particular in the coating or in the (meth)acrylate copolymers of the coating. Substances suitable as plasticizers usually have a molecular weight of between 100 and 20,000 and comprise one or more hydrophilic groups in the molecule, e.g. hydroxyl, ester or ammonium groups. They are frequently esters which are liquid at room temperature: citrates, phthalates, sebacates or castor oil. Examples of suitable plasticizers are alkyl citrates, e.g. triethyl citrate, glycerol esters, alkyl phthalates, alkyl sebacates, sucrose esters, sorbitan esters, diethyl sebacate, dibutyl sebacate and polyethylene glycols 4,000 to 20,000. Preferred plasticizers are triethyl citrate and acetyl triethyl citrate.

Plasticizers may be present for example in amounts of from 5 to 25% by weight based on the polymer or, where appropriate, the polymers of the coating.

Non-Stick Agents:

The silicon dioxide particles present in the coating also assume the function as non-stick agent. Hence, normally and preferably, no further non-stick agents are necessary or present. However, the possible additional use of further non-stick agents is not precluded.

These substances, which usually have lipophilic properties, can be added to the spray suspensions and prevent, in addition to the $SiO_2$ which is present according to the invention, agglomeration of the cores during the film coating. It is possible to employ for example talc or nonionic emulsifiers such as, for example, glycerol monostearate, having an HLB of between 3 and 8. The amounts can be between 1 and 100% by weight based on the polymer. However, care must always be taken that no impairment of the release profile which is desired according to the invention occurs.

Further Excipients

Further pharmaceutically usual excipients which can be added in a manner known per se are, for example, stabilizers, colorants, antioxidants, wetting agents, pore formers, pigments, gloss agents etc.

The ranges described above include all intermediate values and subranges.

Application of the Film Coating:

The application process takes place by means of spray application from organic solution, or aqueous dispersions by melting or by direct powder application. It is crucial for implementation in this case that uniform, pore-free coatings are produced.

For prior art application processes, see, for example, Bauer, Lehmann, Osterwald, Rothgang, "Überzogene Arzneiformen" Wissenschaftliche Verlagsgesellschaft mbH Stuttgart, Chapter 7, pp. 165-196, which is incorporated by reference.

Relevant properties, required tests and specifications for the application are listed in pharmacopoeias.

Details are to be found in customary textbooks which are incorporated by reference, e.g.:

Voigt, R. (1984); Lehrbuch der pharmazeutischen Technologie; Verlag Chemie Weinheim—Beerfield Beach/Fla.—Basle.

Sucker, H., Fuchs, P., Speiser, P.: Pharmazeutische Technologie, Georg Thieme Verlag Stuttgart (1991), especially Chapters 15 and 16, pp. 626-642.

Gennaro, A., R. (Editor), Remington's Pharmaceutical Sciences, Mack Publishing Co., Easton Pa. (1985), Chapter 88, pp. 1567-1573.

List, P. H. (1982): Arzneiformenlehre, Wissenschaftliche Verlagsgesellschaft mbH, Stuttgart.

Active Ingredients (Bioactive Substances):

The invention is suitable for active ingredients which have a solubility in water of at least 10 g/l, preferably at least 30 g/l, particularly preferably of at least 50 g/l, especially preferably of at least 100 g/l, 200 g/l, 300 g/l or 400 g/l at 20° C. (solubility in water based on standard methods such as, for example, Pharmeuropa—Technical Guide for the Elaboration of Monographs, 3rd Edition (1999), Chapter IV, Appendix IV (incorporated by reference) with vigorous shaking for 1 min, leaving to stand for 15 min at 20° C. in purified water). These ranges include all intermediate values and subranges.

The advantageous effects of the invention surprisingly appear not to occur with active ingredients having lower solubility in water, such as, for example, theophylline, with a formulation which is otherwise as claimed.

The pharmaceutical substances employed in the context of the invention are intended to be used on or in the human or animal body in order:

1. to cure, to alleviate or reduce the severity of, to prevent or to diagnose diseases, conditions, physical damage or pathological symptoms.
2. to reveal the condition, the status or the functions of the body, or mental states.
3. to replace active substances or body fluids produced by the human or animal body.
4. to ward off, to eliminate or to render harmless pathogens, parasites or exogenous substances, or
5. to influence the condition, the status or the functions of the body, or mental states.

Conventional pharmaceutical substances can be found in works of reference such as, for example, the Rote Liste or the Merck Index which are incorporated by reference.

It is possible according to the invention to employ all active ingredients which comply with the desired therapeutic effect in the sense defined above and have adequate thermal stability.

The pharmaceutical preparation may comprise for example one or more of the following active ingredients with a solubility in water of at least 10 g/l at 20° C., where appropriate in the form of the water-soluble, pharmaceutically employed salts:

acebutolol, amitryptyline, aripiprazole, atenolol, atropine, betaxolol, bisoprolol, bupavacaine, buprorion, butabarbital, carteolol, carvedilol, cefazoline, cefotaxime, chlorphenaramine, chlorpromazine, clindamycin, codeine, diltiazem, dimercaprol, diphenhydarmine, dopamine, doxylamine, duloxetine, flexainide, fluoxetine, fluphenazine, flurazepam, gentamycin, hydralazine, hydrocortisone, hydroquinone, hyoscyamine, isoniazid, isoproterenol, kanamycin, labetolol, lisinopril, metipranolol, mexiletine, morphine, nadolol, neomycin, norepinephrine, nortryptyline, ondansetron, oxprenolol, oxymetazoline, oxymorphone, paroxetine, penbutolol, phenylephrine, pindolol, prednisolone, primaquine, propranolol, pyrrocaine, sotalol, sulphadiazine, tamoxifen, terbutaline, timolol, tramadol, trazodone, triflupromazine, tetracycline, tubocurarine, venlafaxine and/or verapamil. Particular preference is given to these active ingredients in the form of the water-soluble pharmaceutically employed salts.

Particularly preferred active ingredients for the purposes of the invention are: phenylephrine hydrochloride and terbutaline sulphate.

Administration Forms and Further Embodiments

It is possible in principle for the described pharmaceutical forms to be used directly by oral administration. However, further processing steps preferably follow for multiparticulate forms (multi unit dosage form):

Coated pharmaceutical forms produced according to the invention can be dispensed as single doses into gelatin capsules and bags (sachets) or into suitable multidose containers with metering device. Intake takes place in solid form or suspended in liquids.

Compression of granules, where appropriate after admixture of further excipients, results in tablets which disintegrate after intake and release the slow-release subunits. It is likewise possible to embed agglomerates in polyethylene glycol or lipids to produce suppositories or vaginal pharmaceutical forms.

The outer coatings may additionally be combined or coated also with further prior art coatings. In this special case, the outer coating b) is not the outermost coating. Suitable for this purpose are in particular (meth)acrylate copolymers which comprise 10 to 60% by weight methacrylic acid residues and are otherwise composed for example of methyl methacrylate and/or ethyl acrylate (EUDRAGIT® L or S type). It is possible in this way in combination with the formulations according to the invention additionally to achieve taste-masking properties or formulations for targeted releases in the colon.

Use

The pharmaceutical preparation or composition according to the invention can be used to produce a pharmaceutical preparation or composition or a pharmaceutical form for active ingredients which have a solubility in water of at least 10 g/l at 20° C., with the pharmaceutical form showing sigmoidal active ingredient release characteristics with a lag phase, a pulse phase and a run-out phase, characterized by an active ingredient release in the paddle apparatus at 100 rpm in buffer of pH 6.8 according to the European pharmacopoeia of approximately 10% during the lag phase and a subsequent active ingredient release of approximately a further 80% within less than 4 hours in the pulse phase.

For active ingredient release according to USP, see, in particular, USP 28-NF23, General Chapter <711>, *Dissolution*, Apparatus 2 (Paddle), Method <724> "Delayed Release (Enteric Coated) Articles—General General Drug Release Standard", Method B (100 rpm, 37° C.) (incorporated by reference), but with buffer of pH 6.8 according to the European pharmacopoeia (incorporated by reference).

The sigmoidal active ingredient release characteristics are sufficiently well known to the skilled person, for example from EP-A 0 463 877, EP 1 117 387 B1 and EP-A 0 436 370, all of which are incorporated by reference.

Pharmaceutical Forms

The preparation according to the invention is suitable in a known manner for producing pharmaceutical forms. The preparation may be present for example in pellet form which can be processed by means of pharmaceutically usual excipients and in a manner known per se to multiparticulate pharmaceutical forms, in particular to pellet-containing tablets, mini-tablets, capsules, sachets or reconstitutable powders.

The preparation can preferably be compressed in the form of pellets for example to give a tablet.

The preparation can for example in particular also be in the form of pellets or mini-tablets which are introduced into a gelatin capsule and enveloped thereby.

EXAMPLES

Copolymers Used:
  Copolymer 1:
  65% by weight methyl methacrylate, 30% by weight ethyl acrylate and 5% by weight 2-trimethylammoniumethyl methacrylate chloride (EUDRAGIT® RS).
  Copolymer 2:
  60% by weight methyl methacrylate, 30% by weight ethyl acrylate and 10% by weight 2-trimethylammoniumethyl methacrylate chloride (EUDRAGIT® RL).

The data in Table 1 are based on dry matter.

Solubility of the Active Ingredients in Water:
  Solubility in water based on Pharmeuropa—Technical Guide for the Elaboration of Monographs, 3rd Edition (1999), Chapter IV, Appendix IV (incorporated by reference), with shaking for 15 min, but at 20° C.
  Theophylline: solubility in water=8.4 g/l at 20° C.
  Phenylephrine hydrochloride: solubility in water=500 g/l at 20° C.
  Terbutaline sulphate: solubility in water=500 g/l at 20° C.

TABLE 1

| | Example | | | | | | | | | |
|---|---|---|---|---|---|---|---|---|---|---|
| | 1 | 2 | 3 | 4 | 5 | 6 | 7 | 8 | 9 | 10 |
| Cores | | | | | | | | | | |
| Nonpareilles (600 microns) | 18.13 | 17.12 | 17.12 | 16.66 | 18.97 | 19.55 | 19.05 | 19.22 | 19.05 | 19.55 |
| Na succinate (anhydrous) | 23.53 | 22.22 | 22.22 | 21.62 | 24.62 | | | | 21.86 | 22.73 |
| Succinate | | | | | | 23.46 | 22.86 | 23.06 | | |
| Povidone (PVP K 30) | 2.70 | 2.55 | 2.55 | 2.48 | 2.82 | 2.74 | 2.67 | 2.69 | 2.67 | 2.64 |
| Phenylephrine HCl | 13.89 | 13.11 | 13.11 | 12.76 | 14.53 | | | | | |
| Theophylline | | | | | | 11.73 | 11.43 | 11.53 | | |
| Terbutaline sulphate | | | | | | | | | 12.43 | 10.46 |
| Aerosil 200* | 0.58 | 0.54 | 0.54 | 0.53 | 0.6 | 0.20 | 0.19 | 0.19 | 0.09 | 0.30 |
| Colorant | | | | | | 0.19 | 0.18 | 0.18 | 0.28 | 0.09 |
| Binder | | | | | | 0.27 | 0.27 | 0.26 | 0.27 | 0.37 |
| Coatings | | | | | | | | | | |
| EUDRAGIT ® RS | 26.47 | 25.00 | 25.00 | 24.33 | 27.69 | 23.54 | 22.95 | 34.29 | 22.95 | 23.54 |
| EUDRAGIT ® RL | 2.94 | 2.78 | 2.78 | 2.70 | 3.08 | 2.62 | 2.55 | 3.43 | 2.55 | 2.62 |
| SiO$_2$-244 FP** | 5.88 | 11.11 | | | | | | | | |

TABLE 1-continued

|  | Example | | | | | | | | | |
|---|---|---|---|---|---|---|---|---|---|---|
|  | 1 | 2 | 3 | 4 | 5 | 6 | 7 | 8 | 9 | 10 |
| SiO$_2$-160PQ*** |  |  | 11.11 |  |  | 10.47 |  |  |  | 10.47 |
| Talc |  |  |  | 13.51 |  |  | 12.75 |  | 12.75 |  |
| GMS |  |  |  |  | 1.54 |  |  | 1.71 |  |  |
| Triethyl citrate |  | 5.56 | 5.56 | 5.41 | 6.15 | 5.23 | 5.10 | 6.86 | 5.50 | 5.23 |

Examples 1–3, 10 = According to the invention;
Examples 4 to 9 = Comparative examples
All data in % by weight
*= Colloidal silica, pharmaceutical quality, average particle size about 12 nm
**= SiO$_2$-244FP Syloid ® 244 FP = Precipitated silica, pharmaceutical quality, average particle size about 3 μm
***= SiO$_2$-160PQ = Sipernat ® 160PQ (Degussa AG) = Precipitated silica, pharmaceutical quality, average particle size about 11 μm.

TABLE 2

Table 2: Active ingredient release in buffered medium according to USP in [%]

| Time in h | Example | | | | | | | | | |
|---|---|---|---|---|---|---|---|---|---|---|
|  | 1 | 2 | 3 | 4 | 5 | 6 | 7 | 8 | 9 | 10 |
| 0 | 0.0 | 0.0 | 0.0 | 0.0 | 0.0 | 0.0 | 0.0 | 0.0 | 0.0 | 0.0 |
| 0.5 |  |  |  |  |  | 1.0 | 1.1 | 1.1 |  |  |
| 1 | 0.0 | 0.0 | 0.0 | 0.0 |  | 1.6 | 1.8 | 1.8 |  |  |
| 2 | 0.0 | 0.5 | 0.0 | 0.0 | 0.2 | 3.0 | 3.1 | 2.5 | 0.0 | 0.0 |
| 3 | 0.0 | 0.5 | 0.5 |  | 0.9 |  | 9.7 |  | 0.2 | 0.5 |
| 3.5 | 3.6 | 2.2 | 7.2 |  | 3.3 |  |  |  | 0.8 | 7.2 |
| 4 | 7.3 | 12.0 | 28.1 | 6.3 |  | 10.1 | 17.4 | 11.7 | 14.3 | 32.3 |
| 4.5 | 11.2 |  | 52.2 |  | 8.9 |  |  |  | 25.1 | 58.1 |
| 5 | 17.0 | 60.2 | 68.5 | 3.8 | 14.0 |  |  |  | 42.9 | 72.7 |
| 5.5 |  |  | 79.2 |  |  |  |  |  | 55.7 | 83.0 |
| 6 | 52.7 | 87.3 | 84.1 | 11.7 | 39.0 | 37.9 | 51.8 | 42.8 | 65.1 | 89.1 |
| 7 | 78.6 | 93.6 | 91.2 | 34.9 | 68.2 |  |  |  | 82.3 | 95.8 |
| 8 | 89.7 | 96.0 | 94.3 | 61.6 | 85.7 | 64.8 | 81.2 | 71.7 | 89.1 |  |
| 9 | 94.9 | 98.2 | 96.3 | 78.8 | 93.5 |  |  |  | 92.8 |  |
| 10 |  |  |  | 89.6 |  | 83.8 | 94.4 | 84.3 |  |  |
| 11 |  |  |  | 95.0 |  |  |  |  |  |  |
| 12 |  |  |  | 97.8 |  | 91.8 | 95.6 | 93.7 |  |  |
| Lag [h]* | 4.0 | 4.0 | 3.5 | 6.0 | 4.5 | 4.0 | 3.5 | 4.0 | 4.0 | 3.5 |
| Pulse [h]** | 3.5 | 2.5 | 3.5 | 4.0 | 4.5 | 8.0 | 6.5 | 7.0 | 4.5 | 2.5 |

Examples 1–3, 10 = According to the invention;
Examples 4–9 = Comparative examples
*= Lag [h]: indicates the time of the lag phase in hours, in which up to 10% of the active ingredient are released.
**= Pulse [h]: indicates the time of the pulse phase in hours, in which about a further 80% of the active ingredient are released. The pulse phase in Examples 1, 2, 3 and 10 according to the invention is shortened to less than 4 hours.

The invention claimed is:

1. A pharmaceutical preparation comprising a core that is enveloped by a coating;
   wherein said core comprises an active ingredient, which has a solubility in water of at least 10 g/l at 20° C., and an organic acid, a salt of an organic acid, or both; and
   wherein said coating comprises silicon dioxide particles having an average particle size ranging from 1 to 50 μm, and one or more (meth)acrylate copolymer(s), where at least 60% by weight of said copolymer(s) are free-radically copolymerized units containing 93 to 98% by weight $C_1$- to $C_4$-alkyl esters of acrylic or of methacrylic acid monomers and 2% to 7% by weight (meth)acrylate monomers having a quaternary ammonium group in the alkyl radical;
   wherein said preparation contains said coating in an amount ranging from 10 to 200 wt. % based on the weight of the core; and
   wherein said pharmaceutical preparation exhibits sigmoidal active ingredient release characteristics with a lag phase, a pulse phase and a run-out phase, characterized by an active ingredient release in the paddle apparatus at 100 rpm in buffer of pH 6.8 according to the European pharmacopoeia of approximately 10% during the lag phase and a subsequent active ingredient release of approximately a further 80% within less than 4 hours in the pulse phase.

2. The preparation according to claim 1, wherein said one or more (meth)acrylate copolymers in the coating further comprise:
   1-40% by weight of a (meth)acrylate copolymer which is composed of 85 to less than 93% by weight $C_1$- to $C_4$-alkyl esters of acrylic or of methacrylic acid and more than 7 to 15% by weight (meth)acrylate monomers having a quaternary ammonium group in the alkyl radical.

3. The preparation according to claim 1, wherein the polymer content of the coating consists of a mixture of:
   60 to 99% by weight of a (meth)acrylate copolymer which is composed of 93 to 98% by weight $C_1$- to $C_4$-alkyl esters of acrylic or of methacrylic acid and 2% to 7% by weight (meth)acrylate monomers having a quaternary ammonium group in the alkyl radical, and 1-40% by weight of a (meth)acrylate copolymer which is composed of 95 to 100% by weight $C_1$- to $C_4$-alkyl esters of (meth)acrylic acid and 0-5% by weight (meth) acrylic acid.

4. The preparation according to claim 1, wherein trimethylammoniumethyl methacrylate chloride is present as (meth) acrylate monomer having a quaternary ammonium group in the alkyl radical in the (meth)acrylate copolymer.

5. The preparation according to claim 1, wherein the core, coating, or both comprise(s) at least one pharmaceutically acceptable excipient.

6. The preparation according to claim 1, wherein the lag phase ranges from 3.5 to 4.0 hours and the pulse phase ranges from 2.5 to 4.0 hours.

7. The preparation according to claim 1, wherein the polymer content of the coating together with the proportion of contained $SiO_2$ totals 10 to 100% by weight based on the coating.

8. The preparation according to claim 1, wherein said organic acid is selected from the group consisting of citric acid, fumaric acid, formic acid, acetic acid, maleic acid, succinic acid, tartaric acid, glutaric acid and lactic acid; or their ammonium, lithium, sodium or potassium salts; or mixtures thereof.

9. The preparation according to claim 1, wherein the silicon dioxide particles comprise precipitated silicon dioxide.

10. The preparation according to claim 1, comprising 5 to 50% by weight silicon dioxide particles based on the (meth) acrylate copolymer(s) present in the coating.

11. A tablet comprising the preparation according to claim 1.

12. A gelatin capsule containing the preparation according to claim 1.

13. The preparation according to claim 1, wherein the organic acid and/or the salt of the organic acid forms an outer layer of the core.

14. The preparation according to claim 1, which is enveloped by a (meth)acrylate copolymer which comprises 10-60% by weight methacrylic acid monomers.

15. The preparation according to claim 1, comprising at least one of the following active ingredients or their water-soluble, pharmaceutically acceptable salts: acebutolol, amitryptyline, aripiprazole, atenolol, atropine, betaxolol, bisoprolol, bupavacaine, buproprion, butabarbital, carteolol, carvedilol, cefazoline, cefotaxime, chlorphenaramine, chlorpromazine, clindamycin, codeine, diltiazem, dimercaprol, diphenhydarmine, dopamine, doxylamine, duloxetine, flexainide, fluoxetine, fluphenazine, flurazepam, gentamycin, hydralazine, hydrocortisone, hydroquinone, hyoscyamine, isoniazid, isoproterenol, kanamycin, labetolol, lisinopril, metipranolol, mexiletine, morphine, nadolol, neomycin, norepinephrine, nortryptyline, ondansetron, oxprenolol, oxymetazoline, oxymorphone, paroxetine, penbutolol, phenylephrine, pindolol, prednisolone, primaquine, propranolol, pyrrocaine, sotalol, sulphadiazine, tamoxifen, terbutaline, timolol, tramadol, trazodone, triflupromazine, tetracycline, tubocurarine, venlafaxine, and verapamil.

16. A method for producing a pharmaceutical preparation according to claim 1 comprising:
coating the core with said coating.

17. A method for providing sigmoidal release of at least one active ingredient comprising:
administering the pharmaceutical preparation of claim 1 to a subject in need thereof;
wherein the sigmoidal release constitutes an initial lag phase wherein less than 10% of said active ingredient is released, and a subsequent pulse phase where an additional 80% of said active ingredient is released; and
wherein the pulse phase occurs in less than 4 hours.

18. The method of claim 17, wherein said pharmaceutical preparation is administered orally.

19. A method for treating a disease or disorder comprising administering to a subject in need thereof an effective amount of the pharmaceutical preparation of claim 1.

20. The method of claim 19, wherein said pharmaceutical preparation is administered orally.

21. The preparation of claim 1, wherein said core comprises a nonpareil.

22. The preparation of claim 1, wherein the core further comprises polyvinylpyrrolidone in an amount ranging from 10% to 50% based on the weight of the core.

23. The preparation of claim 1, wherein the core further comprises colloidal silica in an amount ranging from 10% to 50% based on the weight of the core.

24. The preparation of claim 1, wherein the core further comprises polyvinylpyrrolidone and colloidal silica in an amount ranging from 10% to 50% based on the weight of the core and the coating comprises:
Copolymer 1: 65% by weight methyl methacrylate, 30% by weight ethyl acrylate and 5% by weight 2-trimethylammoniumethyl methacrylate chloride; and
Copolymer 2: 60% by weight methyl methacrylate, 30% by weight ethyl acrylate and 10% by weight 2-trimethylammoniumethyl methacrylate chloride.

* * * * *